(12) United States Patent
Calderon et al.

(10) Patent No.: US 9,101,753 B1
(45) Date of Patent: Aug. 11, 2015

(54) ELECTRODE IMPLANT DEVICE

(75) Inventors: Joseph L. Calderon, Arleta, CA (US);
Ross Davis, Melbourne Beach, FL (US);
Delta Mishler, Burbank, CA (US)

(73) Assignee: Alfred E. Mann Foundation For Scientific Research, Santa Clarita, CA (US)

(*) Notice: Subject to any disclaimer, the term of this patent is extended or adjusted under 35 U.S.C. 154(b) by 955 days.

(21) Appl. No.: 12/555,774

(22) Filed: Sep. 8, 2009

Related U.S. Application Data

(63) Continuation-in-part of application No. 11/395,564, filed on Mar. 31, 2006, now abandoned.

(60) Provisional application No. 60/759,219, filed on Jan. 12, 2006.

(51) Int. Cl.
*A61N 1/05* (2006.01)
*A61B 17/34* (2006.01)

(52) U.S. Cl.
CPC .............. *A61N 1/05* (2013.01); *A61N 1/0502* (2013.01); *A61N 1/0504* (2013.01); *A61B 17/3403* (2013.01)

(58) Field of Classification Search
CPC ..... A61N 1/0502; A61N 1/0504; A61N 1/05; A61B 17/3403; A61B 19/201
USPC ................ 606/96, 99, 108, 129; 607/116
See application file for complete search history.

(56) References Cited

U.S. PATENT DOCUMENTS

| 5,060,998 A * | 10/1991 | Phillips ..................... 294/146 |
| 2002/0068912 A1 * | 6/2002 | Merdan ....................... 604/264 |
| 2005/0080400 A1 * | 4/2005 | Corcoran et al. ............. 604/523 |

* cited by examiner

*Primary Examiner* — Thomas McEvoy
(74) *Attorney, Agent, or Firm* — Gary D. Schnittgrund

(57) ABSTRACT

The invention is a hollow electrode implantation device for inserting a flexible electrode, such as a Memberg electrode, in living tissue. The inserter has a longitudinal slot that accepts the electrode into the hollow center of the electrode implantation device. The slot is offset at least once forming one or more offset slots, where retainer tabs define the slots and assure retention of the electrode in the implantation device during insertion of the electrode into living tissue.

6 Claims, 1 Drawing Sheet

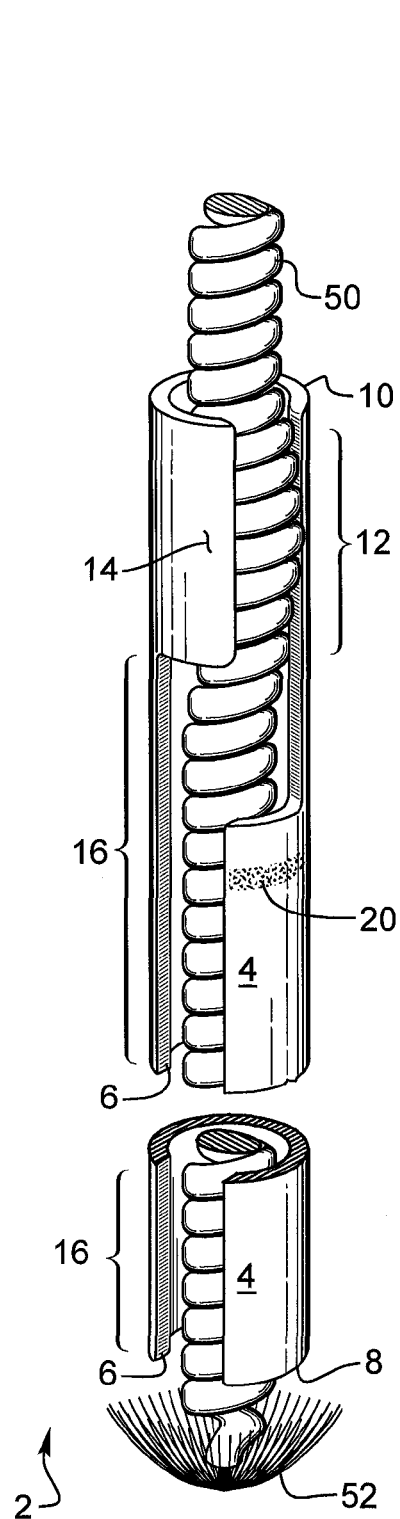
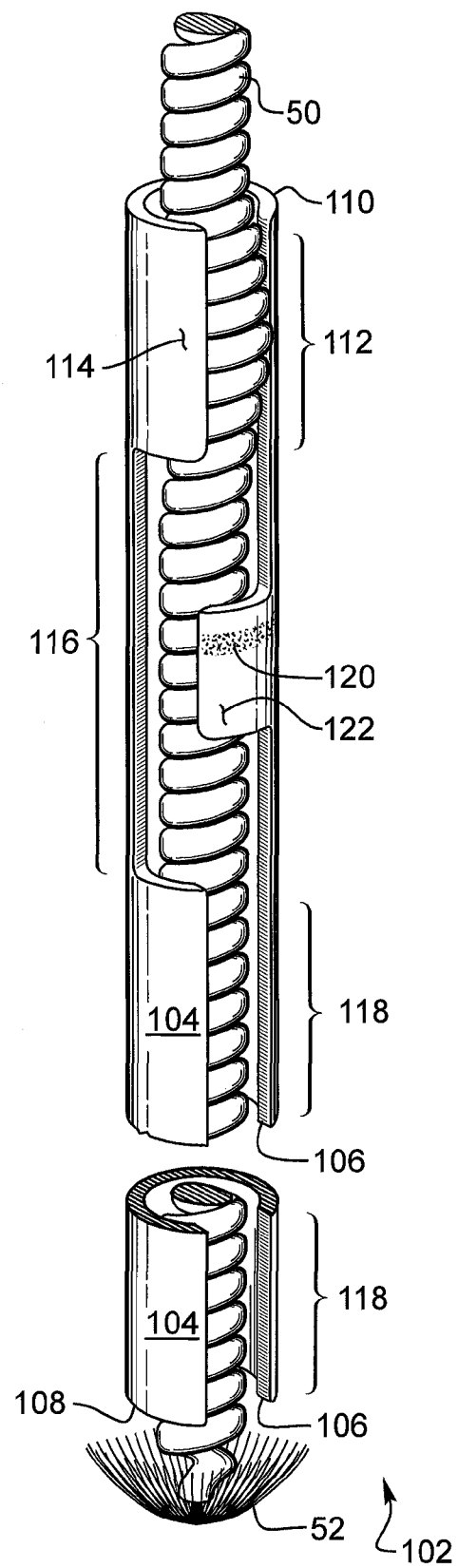
*Fig. 1*
*Fig. 2*

ELECTRODE IMPLANT DEVICE

CROSS REFERENCE TO RELATED APPLICATION

This application is a continuation-in-part of U.S. patent application Ser. No. 11/395,564, filed Mar. 31, 2006; which claims the benefit of U.S. Provisional Application No. 60/759,219, filed on Jan. 12, 2006.

BACKGROUND OF THE INVENTION

1. Field of the Invention

This invention relates to an electrode implantation device for placement of a microstimulator or microsensor in living tissue.

2. Description of Related Art Including Information Disclosed Under 37 CFR 1.97 and 1.98

Microstimulators are small, implantable electrical devices that pass a signal to living tissue in order to elicit a response from a nerve or muscle. Microsensors are similar electrical devices except that they detect electrical and other signals that are generated by living tissue. The term microstimulator applies equally to both microstimulators and microsensors. The use of microstimulators or microsensors which are implanted in living tissue to stimulate a muscle function by either stimulating a nerve or the muscle itself are well known. The microstimulators receive power and control signals by inductive coupling of magnetic fields generated by an extracorporeal antenna rather than requiring any electrical leads. See for example, U.S. Pat. Nos. 5,193,539; 5,193,540; 5,324,316; 5,405,367; 6,175,764; 6,181,965; 6,185,452; 6,185,455; 6,208,894; 6,214,032; and 6,315,721, each of which is incorporated in its entirety by reference herein. These microstimulators are particularly advantageous because they can be manufactured inexpensively and can be implanted by minimally invasive surgery by injection. Additionally, each implanted microstimulator can be commanded, at will, to produce a well-localized electrical current pulse of a prescribed magnitude, duration and/or repetition rate sufficient to cause a smoothly graded contraction of the muscle in which the microstimulator is implanted.

While primarily designed to reanimate muscles so that they can carry out purposeful movements such as locomotion, the low cost, simplicity, safety and ease of implantation of these microstimulators suggests that they may additionally be used to conduct a broader range of therapies in which increased muscle strength, increased muscle fatigue resistance and/or increased muscle physical bulk are desirable; such as therapies directed to muscle disorders. For example, electrical stimulation of an immobilized muscle in a casted limb may be used to elicit isometric muscle contractions that prevent atrophy of the muscle for the duration of the casting period and facilitate rehabilitation after the cast is removed. Similarly, repeated activation of microstimulators injected into the shoulder muscles of patients suffering from stroke enable the paretic muscles to retain or develop bulk and tone, thus helping to offset the tendency for such patients to develop subluxation at the shoulder joint. Use of microstimulators to condition perineal muscles increases the bulk and strength of the musculature in order to maximize its ability to prevent urinary or fecal incontinence. See for example, U.S. Pat. No. 6,061,596, which is incorporated in its entirety by reference herein.

Microstimulators, as exemplified by the BION® of Advanced Bionics Corporation, are typically elongated devices with metallic electrodes at each end that deliver electrical current to the immediately surrounding living tissues. The microelectronic circuitry and inductive coils that control the electrical current applied to the electrodes are protected from the body fluids by a hermetically sealed capsule. This capsule is typically made of a rigid dielectric material, such as glass or ceramic, which transmits magnetic fields but is impermeable to water.

Often, while placing the miniature microstimulator in living tissue, the orientation of the microstimulator changes slightly such that the microstimulator is not in fact in electrical contact with the nerve, requiring reorientation of the microstimulator. The microstimulator may move from the desired location at any point in the surgical implantation procedure. If the microstimulator moves, it may be at a significant distance from the nerve that is to be stimulated or sensed. Consequently, more energy is needed from the microstimulator to stimulate the nerve, unless the microstimulator is repositioned closer to the nerve. While such microstimulators may be injected, the actual placement requires first locating the desired end point near the nerve or muscle. The known method of placement involves locating the nerve with an electric probe, placing a hollow implantation tool over the electric probe and removing the electric probe to allow the miniature microstimulator to be passed down the length of the hollow implantation tool. The implantation tool is then removed, leaving the microstimulator implanted at or near the desired location. If there is a problem with the function or location of the microstimulator, then additional surgery must be performed to remove or relocate the microstimulator, imposing risk, discomfort and potential tissue damage to the patient.

Using a known implantation tool, as disclosed in U.S. Pat. No. 6,214,032, to implant a microstimulator, may lead to the device being located remotely from the desired nerve. In this approach, an electrically stimulating trocar is first used to locate the desired nerve. The trocar is removed, after a cannula is slid along the trocar to be next to the nerve. Then the microstimulator is placed next to the nerve by inserting the microstimulator into the cannula and pushing the microstimulator to the end of the cannula, where it is ejected and is left behind, after the cannula is removed. The problem is that once the electrically stimulating trocar is removed, there is no way to detect movement of the cannula. Thus, the microstimulator may be left some distance from the desired location, as was determined by the stimulating trocar. This displacement from the optimum stimulating site unacceptably increases the power requirements and diminishes the battery life of the microstimulator.

Know devices such as that disclosed by Skakoon, US Pat. Publication US 2004/0044348, published Mar. 4, 2004, appear at first glance to provide a similar function. However, the device taught by Skakoon provides a means of retaining a medical electrical lead for passing through living tissue. It provides no method for removing the lead for implantation in living tissue. Further, it does not benefit from and provides no indication of depth of insertion into the living tissue since it passes completely thorough the tissue and does not teach implantation of the electrode in living tissue. The device taught by Skakoon teaches no means for retention of a flexible electrode during insertion since the device provides a single, collinear longitudinal slot with two fingers that cannot retain a flexible electrode lead in the device. Skakoon teaches that a portion of a catheter or a shunt or a medical electrical lead electrically conducting wire passes through the living tissue and that electrode terminates outside of the living tissue body, where it can be attached to another device. After passing through the tissue and not while within the tissue, the electrode is removed from the insertion device by moving the lead in a direction that is perpendicular to the longitudinal axis of the device.

Therefore, it is desired to have a method of implantation of a flexible electrode that ensures that the microstimulator is properly located and is implanted in an optimum position prior to removing the electrode implantation tool that is utilized during surgery to place the electrode lead.

GLOSSARY

Terms are to be interpreted within the context of the specification and claims. The following terms of art are defined and shall be interpreted by these definitions. Medical terms that are not defined here shall be defined according to The American Heritage Stedman's Medical Dictionary, Houghton Mifflin, 1995, which is included by reference in its entirety. Terms that are not defined here shall be defined according to definitions from the ASM Metals Reference Book, $3^{rd}$ Edition, 1993, which is included by reference in its entirety.

Biocompatible. The ability of a long-term implantable medical device to perform its intended function, with the desired degree of incorporation in the host, without eliciting any undesirable local or systemic effects in that host. Regulatory agencies require that implanted objects or devices within the human body be biocompatible.

Body. The entire material or physical structure of an organism, especially of a human.

Cavity. The hollow area within the body, such as a sinus cavity, vagina, mouth, anus, or ear.

Electrode. A flexible, biocompatible electrical conductor, such as a Memberg electrode.

Electrode Lead. See electrode.

Hermetic. Completely sealed by fusion, soldering, brazing, etc., especially against the escape or entry of air or gas.

Implant. To embed an object or a device in a body surgically along a surgically created implantation path.

Insert. To place an object or a device into a body cavity.

Microstimulator. An implantable, biocompatible device having dimensions that are less than about 6 mm diameter and 60 mm in length that is capable of sensing or stimulating electrical signals within living tissue.

Subcutaneous. Located, found, or placed just beneath the skin.

Surgery. A procedure involving the cutting or intrusive penetration of body tissue by cutting or penetration and not by inserting an object or a device into a naturally existing body cavity.

Surgical. Of, relating to, or characteristic of surgeons or surgery.

BRIEF DESCRIPTION OF THE SEVERAL VIEWS OF THE DRAWINGS

FIG. 1 schematically depicts a perspective view of the electrode implant device with one retainer tab and one offset slot showing the electrode inserted inside the hollow tube.

FIG. 2 schematically depicts a perspective view of the electrode implant device with two retainer tabs and two offset slots showing the electrode inserted inside the hollow tube.

DETAILED DESCRIPTION OF THE INVENTION

An electrode implantation device 2 is presented generally in FIG. 1 which comprises a hollow tube 4 having a thin wall 6. A longitudinal offset slot 12 begins at the proximal end 10 of the hollow tube 4 and extends with an approximately constant width longitudinally along the wall 6. The offset slot 12 is defined by a retainer tab 14, said offset slot 12 accepting a flexible and implantable electrode 50, where in a preferred embodiment electrode 50 is a Memberg electrode, as is known in the art, having a distal end 52 that is designed to aid in retention of the Memberg electrode 50 after insertion in living tissue.

Said offset slot 12 jogs in an interrupted fashion to form a continuous longitudinal opening in the wall 6, defined as a retainer slot 16, extending to a distal end 8 of said electrode implantation device 2. The offset slot is not collinear, but consists of two longitudinal centers which are separate from, that is offset from each other to provide for retention of a flexible electrode 50. The electrode 50 is urged into said retainer slot 16 and into said offset slot 12, being retained in that position by retainer tab 14.

The electrode implantation device 2 has a depth mark 20 on the outside of the tool 2 which provides a visual reference to the desired depth of penetration of the tool 2 into living tissue.

The electrode implantation device 2 enables a surgeon to insert the electrode more easily than with known insertion tools, which have proven to be cumbersome and which require the use of two hands to retain or replace the electrode in the insertion tool during implantation.

An alternate embodiment of the electrode implantation device 102 is presented in FIG. 2. To assure retention of the electrode 50 a second retainer slot 118 is added. The electrode implantation device 102 comprises a hollow tube 104 having a thin wall 106. A longitudinal offset slot 112 begins at the proximal end 110 of the hollow tube 104 and extends with an approximately constant width longitudinally along the wall 106, jogging to form retainer slot 116. The offset slot 112 is defined by a second retainer tab 114 and a center retainer tab 122, which keep the electrode 50 in the hollow tube electrode implantation device 102 during implantation.

Said offset slot 112 jogs in an interrupted fashion to form a continuous longitudinal opening in the wall 106. The retainer slot 116 jogs or is offset and not collinear to form second retainer slot 118 which extends to the distal end 108 of hollow tube 104. The electrode implantation device 102 has a depth mark 120 on the outside of the tool 102 as a visual reference to the desired depth of penetration of the tool 102 into living tissue.

When the electrode implantation device 2, 102 is withdrawn from the living tissue along the insertion path, the electrode 50 remains in position in the living tissue, near the target nerve, for example. The electrode 50 is removed from the tissue with minimal disruption to the living tissue and the electrode is removed from the implantation device 2 after the device 2 is withdrawn from the tissue along its insertion path. The electrode remains in location near a target nerve, for example, in the living tissue by virtue of the electrode sliding longitudinally along the implantation device 2 as the device is withdrawn from the living tissue. The electrode 50 is restricted in movement, while resident in the electrode implantation device 2, to moving or sliding along the longitudinal axis of the implantation device 2 and cannot move perpendicular to the longitudinal axis of the implantation device 2. As discussed, the electrode is retained in the implantation device by virtue of the offset slots 12, 112. Post-surgery the implantation device is withdrawn from the single insertion point and is readily removed from the flexible electrode.

What is claimed is:

1. An electrode implant device comprising:
   an electrode implant tool and an implantable electrode, the electrode implant tool having an exterior surface and an interior lumen;
   the electrode implant tool comprising:
   a rigid hollow tube comprised of a thin wall and having a longitudinal axis defining at least one longitudinal offset slot wherein said offset slot comprises two longitudinal opening portions in the wall which are laterally offset from each other and which form a continuous longitudinal opening in the wall thereby retaining the electrode; and at least one retainer slot for accepting and retaining the electrode in the interior lumen of the electrode implant tool;

said longitudinal offset slot having a constant and fixed width along said thin wall;

said longitudinal offset slot being fixedly open to the exterior surface of said electrode implant tool; and an integral hollow tube retainer tab defining a portion of the at least one offset slot and a portion of the at least one retainer slot to retain the electrode in said tube and to restrict movement of the electrode within the electrode implant tool to movement along the longitudinal axis.

2. The electrode implant device according to claim 1, further comprising a second retainer slot in the electrode implant tool for securing the electrode in said rigid hollow tube.

3. The electrode implant device according to claim 1, further comprising a depth mark on said hollow tube to define a position of said electrode implant tool.

4. An electrode implant device comprising:

an electrode implant tool and an implantable electrode, the electrode implant tool having an exterior surface and an interior lumen;

the electrode implant tool comprising:

a rigid hollow tube having a longitudinal axis, continuously open longitudinal offset slot of fixed width and a retainer slot of sufficient length for receiving the electrode through said longitudinal offset slot and said retainer slot to position the electrode within said hollow tube wherein said longitudinal offset slot is fixedly open to the exterior surface of said electrode implant tool;

said longitudinal offset slot and said retainer slot of constant and fixed width are offset laterally from each other, not in collinear alignment, forming one or more offset slots, wherein an at least one retainer tab defines said slots and assures retention of the electrode in the interior lumen of the electrode implant tool, during insertion of the electrode into living tissue; and said at least one retainer tab positioned along the length of the rigid hollow tube intermediate the slots and dimensioned to permit entry of the electrode into the tube and to maintain the electrode in the rigid hollow tube, once the electrode is positioned therein, such that the electrode movement is restricted to the direction of the longitudinal axis.

5. The electrode implant device according to claim 4, further comprising a second retainer slot in said electrode implant tool for securing the electrode in said rigid hollow tube.

6. The electrode implant device according to claim 4, further comprising a depth mark on said, rigid hollow tube to define a position of said electrode implant tool.

* * * * *